Figure 1:
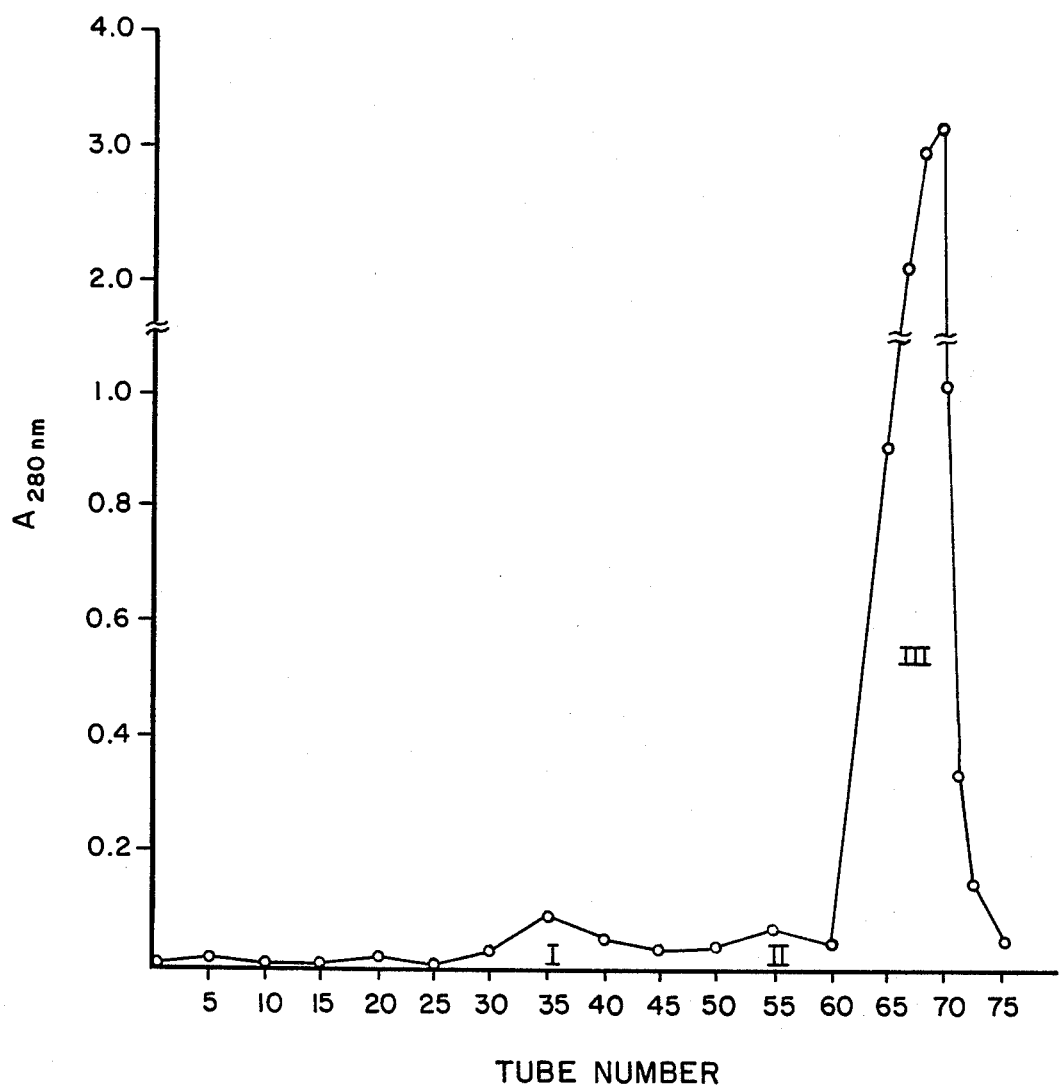

United States Patent [19]

Jacobson

[11] Patent Number: 4,770,877
[45] Date of Patent: * Sep. 13, 1988

[54] ISOLATION OF A HIGH MOLECULAR WEIGHT AORTIC ENDOTHELIAL CELL GROWTH INHIBITOR

[75] Inventor: Bernard Jacobson, Lexington, Mass.

[73] Assignee: Boston Biomedical Research Institute, Boston, Mass.

[*] Notice: The portion of the term of this patent subsequent to Dec. 1, 2004 has been disclaimed.

[21] Appl. No.: 758,552

[22] Filed: Jul. 24, 1985

Related U.S. Application Data

[63] Continuation-in-part of Ser. No. 404,656, Aug. 3, 1982, Pat. No. 4,534,967.

[51] Int. Cl.$^4$ ................. A61K 35/44; A61K 37/00
[52] U.S. Cl. ........................................ 424/95; 514/2
[58] Field of Search ........................... 424/95; 514/2

[56] References Cited

U.S. PATENT DOCUMENTS

| | | | |
|---|---|---|---|
| Re. 30,239 | 2/1980 | Kuettner et al. | 424/95 |
| 3,864,084 | 2/1975 | Folkman | 23/230 |
| 4,042,457 | 8/1977 | Kuettner et al. | 424/95 |
| 4,164,560 | 8/1979 | Folkman et al. | 424/19 |
| 4,176,177 | 11/1979 | Kuettner | 424/95 |
| 4,217,412 | 8/1980 | Tolbert et al. | 435/68 |

OTHER PUBLICATIONS

Raymond et al.,-ARVO Abst. (Apr. 1980), Abst 8-10:15, pp. 145-146.
Jacobson et al.-ARVO Abst. (Mar. 1981), Abst. 46, p. 216.
Raymond et al.-Exp. Eye Res., vol. 34.000-00, Feb. 1982.
"Isolation and Identification of Stimulatory and Inhibitory Cell Growth in Bovine Vitreous", by Laurie Raymond et al., *Academic Press Inc.*, 1982, 34. 000-000.
G. A. Lutty et al., J. Cell Sci., 76, 53-65, (Jun. 1985).

*Primary Examiner*—Sam Rosen
*Attorney, Agent, or Firm*—Weingarten, Schurgin, Gagnebin & Hayes

[57] ABSTRACT

Liquified vitreous gel, prepared by a non-extractive technique, has been found to contain a cell proliferation inhibitor whose molecular size is greater than 10,000 daltons. Vitreous isolated from both bovine and chick embryo sources has been found to contain such an activity, which inhibits the growth of endothelial cells prepared from calf aorta. Culture medium conditioned by exposure to calf vitreous hyalocytes (cells found on the periphery of the vitreous gel), is also a source of the high molecular weight inhibitor.

The high molecular weight inhibitor is prepared by chromatography of vitreous or hyalocyte-conditioned medium on a column of Bio Gel P-10 or by ultrafiltration. Mateial appearing in the void volume of Bio Gel P-10 (the material whose molecular size is too large to allow it to enter the gel) has a molecular size greater than 13,000 daltons. Ultrafiltration is carried out using a filter whose molecular size cut-off point is 10,000 daltons, therefore material which is retained by the filter has a molecular size of 10,000 daltons and above.

15 Claims, 4 Drawing Sheets

ISOLATION OF A HIGH MOLECULAR WEIGHT AORTIC ENDOTHELIAL CELL GROWTH INHIBITOR

BACKGROUND OF INVENTION

This is a continuation-in-part of application Ser. No. 404,656 filed Aug. 3, 1982, which is incorporated herein by reference, now U.S. Pat. No. 4,534,967.

This invention relates to a method of preparing an inhibitor of endothelial cell growth. The products of this method are useful in treating or preventing ocular neovascularization and reducing neovascularization in tumors.

Endothelial cells are a key component of blood vessels. Proliferation of vascular endothelial cells plays an important role in many biological processes. These include wound healing, formation of inflammatory granulation tissue, the organization of thrombi, the healing of large vessel defects and the repopulation of endothelium in grafts. Normal adult vascular endothelium represents a slowly renewing population of cells. However, several pathological situations result in abnormal endothelial cell proliferation with the formation of unwanted new blood vessels. This latter process is called "neovascularization".

Neovascularization of ocular tissues is one of the most important clinical problems in ophthalmology. In many disease states the various mature vascular beds of the eye grow beyond their normal limits. Diabetes mellitus is responsible for loss of vision in 12% of the total United States blind population and for 20% of the cases of new blindness in adults between the ages of 45 and 74. Retinopathy, the major cause of blindness in diabetics is responsible in about 84% of blind diabetic patients. At some critical point capillary endothelium begins to proliferate. The new retinal vessels may penetrate the internal limiting membrane of the retina and enter the vitreous where devastating hemorrhages may occur, leading to blindness. During the active, proliferative phase of diabetic retinopathy, neovascularization is also accompanied by fibrous tissue formation, which, when connected between the retinal and vitreous surfaces, can produce tractional elevation and tearing of the retina with subsequent retinal detachment. In the case of diabetic retinopathy, hemorrhage into the vitreous caused by traction on the new blood vessels is treated by removal of the vitreous. Retinal detachment is also sometimes treated by surgery.

The growth of solid tumors has long been recognized to be dependent on the ability of the tumor to induce the formation of new blood vessels by their hosts. The host blood vessels vascularize the solid tumor and provide it with nutrients which allows continued tumor growth.

A cell proliferation inhibitor has been prepared from liquified vitreous gel (Raymond and Jacobson "Isolation and Identification of Stimulatory Cell proliferation" *Exp. Eye Res* 34, 267–86 (1982). This inhibitor has a molecular weight of approximtely 6,000 daltons.

One object of this invention is to provide a novel inhibitor of endothelial cell growth having a molecular weight of over 10,000 daltons.

Another object of this invention is to provide such an inhibitor which will prevent neovascularization in ocular tissue and solid tumors.

Still another object of this invention is to reduce the need for surgery in diabetic retinopathy.

Further objects and advantages of this invention will be apparent from the description and claims which follow.

SUMMARY OF INVENTION

This invention comprises broadly preparing a cell proliferation inhibitor by a non-extractive method from a tissue which has neither a high content of collagen, nor proteoglycans. An example of such tissue is the vitreous body including human and animal vitreous. The inhibitor is isolated directly from the vitreous by chromatography, as for example, liquid chromatography. The chromatography fraction having a molecular weight above 10,000 daltons has been shown to have a particular marked inhibitory effect on the rate of proliferation of endothelial cells. Another source of inhibitor comprises hyalocyte cells, which release the inhibitor into culture medium.

The method of this invention comprises freezing the vitreous gel for a sufficient time so as to inactivate growth stimulators that may be present. This may be accomplished by continuous freezing or subjecting the vitreous gel to alternate freeze/thaw cycles. The gel is then directly liquefied in the absence of extraction solvent by application of shear forces to the gel so as to directly convert the gel into a liquid, removing any insoluble and suspended material from the liquid, chromatographically separating the liquid into fractions of varying molecular weight and isolating a product of molecular weight in excess of 10,000 daltons which has inhibitory activity.

The cell proliferation inhibitor of this invention when administered to ocular tissue by appropriate opthalmalogical procedures is useful in arresting the neovascularization which accompanies diabetic retinopathy.

Also, the cell proliferation inhibitor of this invention when implanted in the area of solid tumors causes the tumors to become dorment or to shrink. It is believed that after application of the inhibitor, the tumors may be more susceptible to conventional chemotherapy or radiotherapy.

In order to obtain enough material for use, chick embryo vitreous was stored frozen for several months prior to use, while the human (Eye Bank) vitreous had been frozen prior to lyophilization, and the lyophilized material stored below freezing prior to assay. In previous studies, fresh adult bovine vitreous which had remained at 4° C. for 16-20 hrs was used or, vitreous which had been kept frozen for only one week and thawed only once. When high molecular weight (P-10 void volume) endothelial cell growth inhibitory activity was demonstrable in chick embryo and human vitreous which had been kept frozen (as well as in hyalocyte-conditioned medium which had also been stored frozen), fresh versus frozen bovine was re-examined. As will be shown below, the use of material which had been kept frozen for 8-10 months or had gone through several freeze-thaw cycles showed inhibitory activity in the P-10 void volume and in the early-eluting retarded volume fractions, while freshly-prepared adult bovine vitreous again showed a stimulatory activity in the material appearing in the void volume.

SPECIFIC EXAMPLES OF INVENTION

Preparation of Vitreous

The posterior portion of the vitreous, which is a clear gel, is removed from the bovine eyes. It is then forced through a small orifice (e.g. through a syringe). The resultant material is liquid. The liquid is then centrifuged to remove any tissue debris, cells and the small amount of insoluble collagen. The product may be kept frozen at $-20°$ C., unless used within an 18hour period, in which case it may be kept at $+4°$ C.

Liquid Chromatopraphy Fractionation

Bio Gel p-10 or porous glass beads are preferred. "Bio-Gel P-10" is a commercial polyacrylamide spherical beaded gel sized in particle sizes to permit fractionation in the range of 1,500 to 20,000 daltons. Other suitable media for gel filtration chromatography include ion exchange cellulose chromatography or ion exchange gel chromatography. The vitreous liquid may be concentrated prior to column fractionation by placing it in cellulose tubing of 3,500 dalton cut-off point and covering the tubing with a dry material, such as polyethylene glycoi, which draws the water out of the tubing. The vitreous liquid is then loaded onto a chromatographic column containing the Bio-Gel P-10 and eluted with physiological saline, 0.15-M NaCl. The fractions eluted from the column are assayed for ultraviolet absorption at 280 nm. Fractions eluted from the column are mixed with serumcontaining tissue culture medium, sterile filtered and added to endothelial cells to test their effect on cell proliferation.

Endothelial Cell Preparation

Vascular endothelial cells were prepared from calf aorta by the method of Macarak, et al. (Macarak, E. J. Howard, B. V., and Kefalides, N. Lab. Invest.36, 62–67, (1977).) including treatment of the aortas with a tissue culture medium containing the enzyme collagenase. The endothelial cells were collected in a tissue culture medium e.g. Dulbecco's Modified Eagles Medium (DMEM) containing 10% newborn calf serum (NBCS) plus penicillin, streptomycin and fungizone. The cells were then transferred to culture flasks or dishes and allowed to proliferate in culture medium, and then transferred to 24-well plates for testing of the inhibitory factor. All cell cultures were kept in a humidified $CO_2$ incubator (5% $CO_2$ in air) at 37° C.

Assay of Inhibition of Cell proliferation.

The assay procedure was based on cell proliferation being necessarily accompanied by the synthesis of new DNA. One of the constituents of DNA is the nucleoside thymidine. Addition of radioactive thymidine to the cell culture medium results in uptake of radioactive thymidine by the cells and its subsequent incorporation into newly synthesized DNA. A reduction of radioactive thymidine incorporation into newly synthesized DNA is indicative of a reduction in cell proliferation.

Fractions from the column fractionation of vitreous described above were mixed with culture medium in concentrations ranging from 10–40% V/V, sterile filtered and added in amounts of 0.5 cc per well to duplicate sets of wells already containing the cell type to be tested in 0.5 cc of culture medium. After 24 hours, 0.50 cc were removed from each well and a fresh aliquot of 0.50 cc of the fractions to be tested were added to the wells containing the cells. At the same time, 1 microcurie of radioactive thymidine (tritium-labelled) were also added to each well and the cells allowed to incubate for an additional 24 hours. The culture medium was then removed from the cell layer, the cells were briefly washed with fresh culture medium and 0.5M NaOH was added to each well for 8 hours at 37° C. (This treatment extracted DNA from the cells) The contents of each well were transferred to separate test tubes and mixed with nonradioactive DNA (0.5 mg/tube). DNA (mixture of radioactive and non-radioactive) was then precipitated by addition of trichloroacetic acid (final concentration 30%) and collected on 0.45 um pore size filters. The filters were dissolved in a solvent (e.g. Filtron X) and the radioactive DNA assayed in a liquid scintillation spectrometer. The amount of radioactive DNA in the cells treated with the various column fractions was compared to control cell cultures which received 0.15M NaCl.

Hyalocyte cultures

Calf eyes were trimmed of surrounding connective tissue, rinsed in running cold tap water and soaked for 30 minutes in a bactericidal/fungicidal solution (Duet, Madison Bionics). After rinsing the eyes again in distilled $H_2O$, the posterior gel, containing the hyalocytes was isolated essentially as described by Balazs, Toth, Eckl and Mitchel (1964). The gel pieces were passed through a syringe (without a needle) to break the gel. The vitreous, containing the hyalocytes, was then incubated with sterile-filtered collagenase (1 mg/cc, Type III, Worthington Biochemical Corp.) and leech hyaluronidase (1 mg/cc, Biomatrix) in Earle's Basal Medium BME containing Earle's salts (GIBCO), glutamine, 20 mM-Na pyruvate instead of glucose, 20 mM-Hepes, vitamins and Gentamicin, without serum at 37° C. until inspection showed the vitreous to be significantly reduced in viscosity. At this point the cells were isolated by centrifugation at 1000 r/min in a Beckman TJ-6 centrifuge for 10 min., suspended in fresh BME and kept for 18 hr. without shaking in humidified 5% $CO_2$ in air. Each separate tube included cells from two eyes. After 18 hours the cells were separated from the culture medium by centrifugation as described above. The medium was mixed with DMEM/10% NBCS, sterile filtered and added to wells, containing the cells on whose growth the conditioned medium was to be tested, in the range of concentrations and amounts/well described above. Cell viability of the hyalocytes was well maintained up to at least 18 hours as demonstrated by the cells' 95% exclusion of trypan blue.

EXAMPLES OF INVENTION

The preparation of calf aortic endothelial cells, liquid adult bovine vitreous and assay of stimulation and inhibition of growth of aortic endothelial cells by measuring thymidine incorporation into DNA all utlized methods described above. Fresh vitreous refers to material which was allowed to remain at 4° C. overnight following isolation. Twenty-twenty five ml were concentrated to 5–8 ml in 3,500 dalton cutoff dialysis tubing (Spectrapore, Spectrum Medical Industries) at 4° by covering the tubing with Aquacide (Calbiochem-Behring). Bovine vitreous was separated into high and low molecular weight components by chromatography at 4° C. on a 0.9 cm × 104 cm column of Bio Gel P-10. The column was eluted with 0.15 NaCl, collecting 4 ml fractions. Aliquots of column fractions were prepared for testing in cell culture as described above. Two consecutive column fractions were pooled, sterile filtered, mixed with culture medium and added to aortic endothelial cells in duplicate cultures. Control duplicate wells received medium plus a volume of 0.15M NaCl equal to the vitreous fraction tested. Levels of stimulation or inhibition were determined by comparison of the means of each set of duplicate cultures. Standard deviations were calculated and a fraction was judged to be stimulatory or inhibitory only if there was no overlap between control and test values.

Liquid vitreous was also subjected to ultrafiltration at 4° C. using an Amicon model 8200 stirred ultrafiltration cell together with Amicon YM-10 filter. The material retained by the filter (>10K fraction) was removed from the filter by shaking with distilled water for 24 hours at 4° C., after which the solution was lyophilized and then stored at −20° C. In most experiments the YM-10 ultrafiltrate (<10K fraction) was dialyzed in 3,500 dalton cutoff tubing at 4° C. for 24 hours against distilled water, after which it was lyophilized and stored below freezing as described above. The ultrafiltrate was also fractionated on a large (3 cm×82 cm) column of Bio Gel P-10. Elution was monitored by 280 nm absorption and peaks were pooled, dialyzed in 3,500 dalton cutoff tubing and lyophilized as described above. When the high and low molecular weight fractions from ultrafiltration were dissolved for ion exchange gel filtration chromatography, they were first subjected to three freeze-thaw cycles using a dry ice-2 propanol bath. Anion and cation-exchange gel filtration chromatography was carried out using DEAE-Sephadex A-25. OAE-Sephadex A-25, CM-Sephadex C-25 and SP Sephadex C-25 (all from pharmacia). Each was suspended in 0.01M KCl and packed as 1.2 cm×98 cm columns. After the various vitreous samples to be fractionated were applied to the columns at 4° C., each column was washed with a volume of 0.01M KCl equal to the column void volume. At this point a gradient was begun with 250 ml 0.01M KCl in the mixing vessel and 250 ml 2M KCl in the reservoir. 4 ml fractions were collected at a flow rate of approximately 7.2 ml per hr. Column eluates were monitored by ultraviolet absorption at 280 nm, and, in some cases, by carbazole uronic acid colorimetric analysis at 530 nm (8). The material eluted by the gradient was dialyzed in 3,500 dalton cutoff tubing against distilled water at 4° C. and then lyophilized. The dry material was dissolved in 0.15M NaCl and sterile filtered through 0.22 μm filters (Gelman) prior to analysis for inhibitory activity in cell culture. Chromatofocusing was carried out on 1 cm×30 cm column of PBE 94 (pharmacia). The PBE 94 was equilibrated with ten column volumes of start buffer, 0.025M imidazole-HCl, pH 7.4 On the top of the column was layered 2 cm of Sephadex G-25. The amphoteric Polybuffer 74 (pharmacia) was diluted 1:8 with distilled water and the pH was adjusted to 4 with HCl. The material applied to the column was eluted at a flow rate of 7 ml/hr and collected in 4 ml fractions. After application of the vitreous material to be fractionated (dissolved in start buffer), the column was eluted with 2.5 column volumes of start buffer followed by 11.5 column volumes of polybuffer 74. In order to remove strongly bound material, the column was washed with 1M NaCl followed by 0.1N HCl before re-equilibration with start buffer. Protein elution was monitored at 280 nm. protein peaks were dialyzed (3,500 dalton cutoff tubing), lyophilized and then dissolved in 1 ml distilled water. protein was separated from Polybuffer 74 by chromatography on a 0.9 cm x 126 cm column of Sephadex G-75 (Pharmacia) eluted with 0.15M NaCl.

RESULTS

1. Presence of Inhibitory Activity in High and Low Molecular Weight Forms

The demonstration of inhibitory activity in the material excluded from Bio Gel P-10 is dependent on the loss of activity of a stimulatory factor present in freshly prepared bovine vitreous, either through extended freezing or several freeze-thaw cycles. When freshly prepared bovine vitreous was chromatographed on Bio Gel P-10, endothelial cell growth stimulatory activity was present in two pooled fractions representing the excluded volume (Table I). In Table II are presented the results obtain when an aliquot of P-10 void volume fractions, which had been pooled from several column runs and kept frozen for almost one year, was added to aortic endothelial cell cultures. As can be seen, an inhibitory effect was now evident.

When the low molecular weight ultrafiltrates (<10K fraction), prepared from vitreous which had been frozen and thawed several times, was passed over a preparative column of Bio Gel P-10, three areas of inhibitory activity were seen (Table 111). The presence of multiple areas of inhibitory activity in the low molecular weight fraction agrees with our previous results obtained with human vitreous (Jacobson, B., Basu, P. K. and Hasany, S. M. (1984). Vascular endothelial cell growth inhibitor of normal and pathological human vitreous. Arch. Ophthalmol. 102, 1543–1545), chick embryo vitreous and hyalocyte-conditioned medium (Jacobson, B. Dorfman, T., Basu, P. K., and Hasany, S. (1985). Inhibition of vascular endothelial cell growth and trypsin activity by vitreous. Exp. Eye Res. In press. ).

11. Ion exchange—Gel Chromatograghy of Vitreous Inhibitors a. Low molecular weight fraction.

Two experiments in which the vitreous ultrafiltrate was chromatographed on CM-Sephadex C-25 resulted in all of the inhibitory activity being present in the material which did not bind and was eluted with 0.01M KCl (Table IV). Chromatography on DEAE-Sephadex A-25 (FIG. 1) produced three areas of inhibitory activity (Table V). As peak 11 contained the strongest inhibitory activity, but was extremely low in protein, this step results in a significant purification of the vitreous ultrafiltrate inhibitory activity.

b. High molecular weight fraction.

Figure 2:
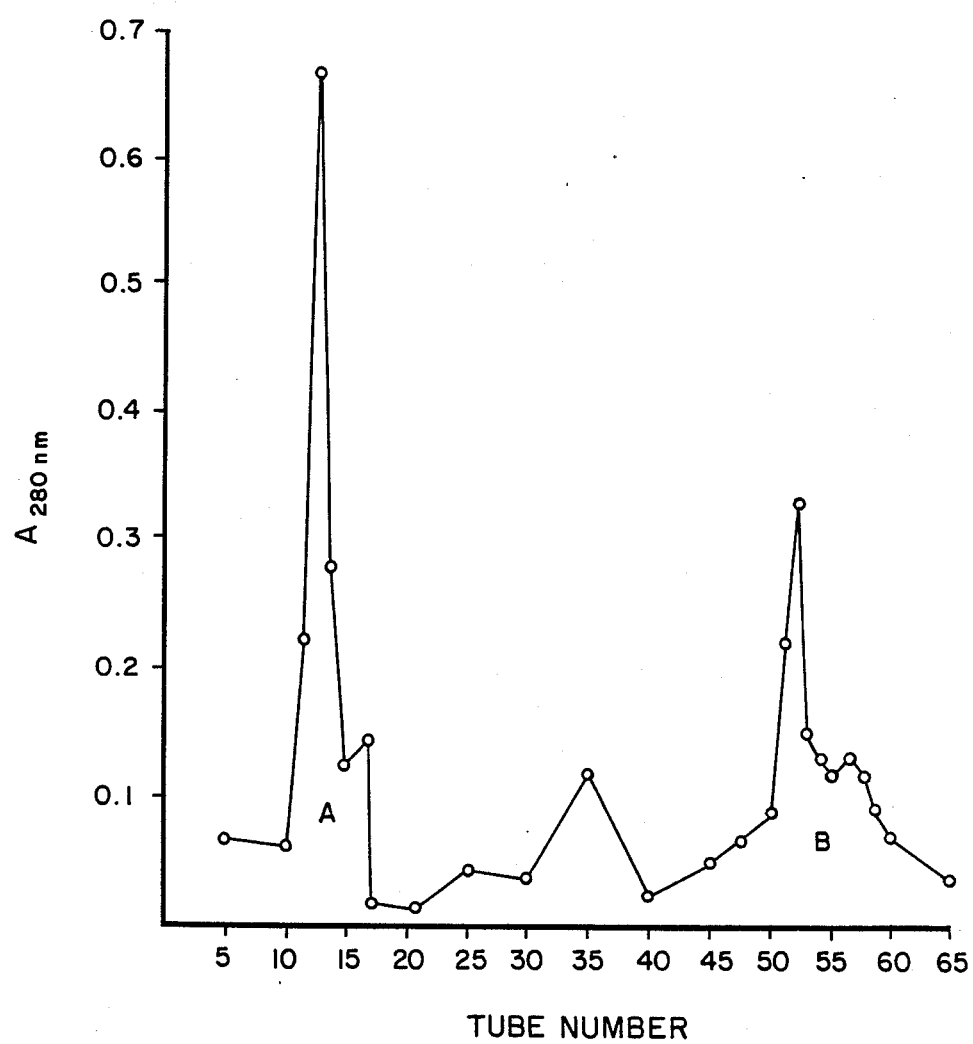
Figure 3:
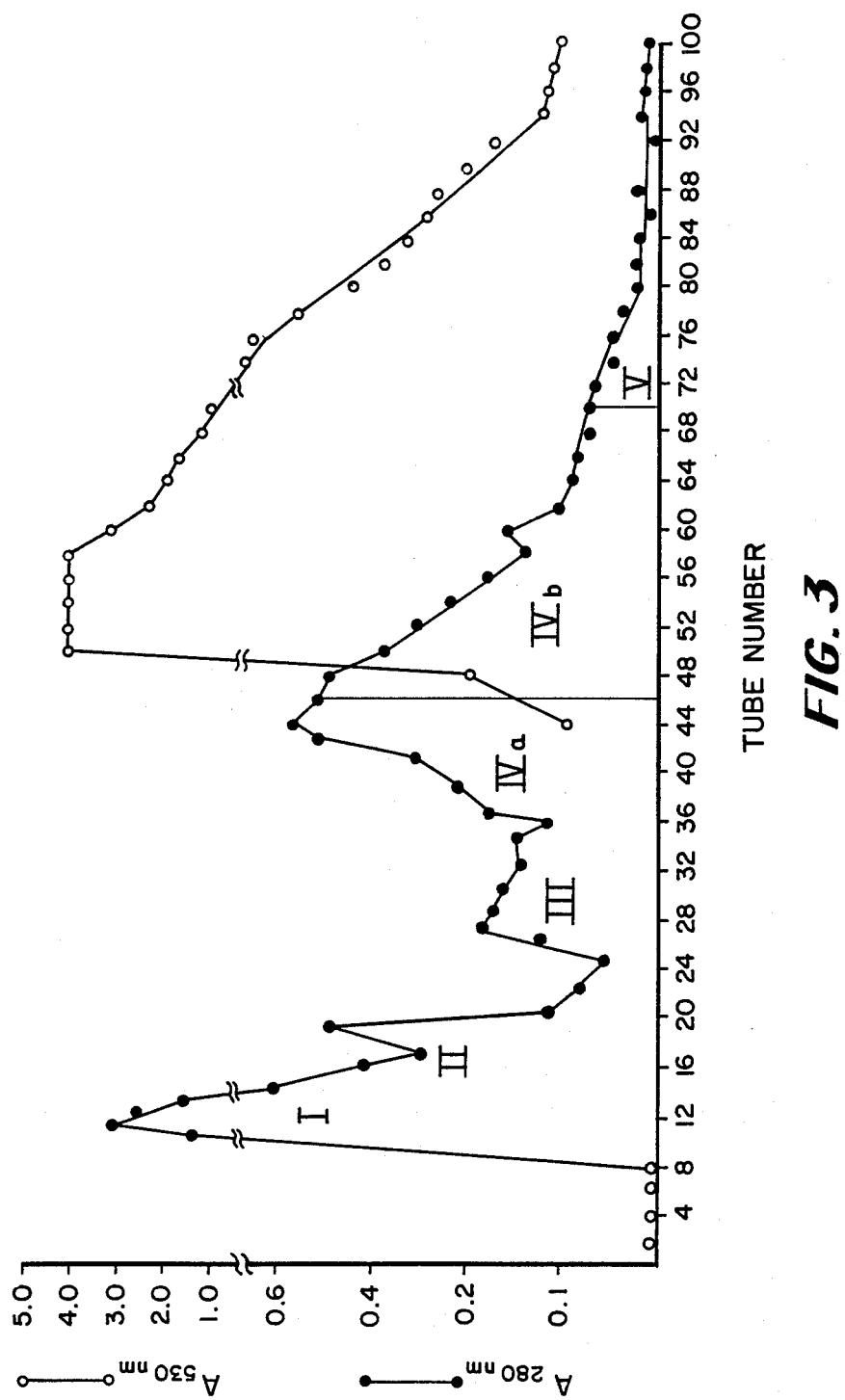
Figure 4:
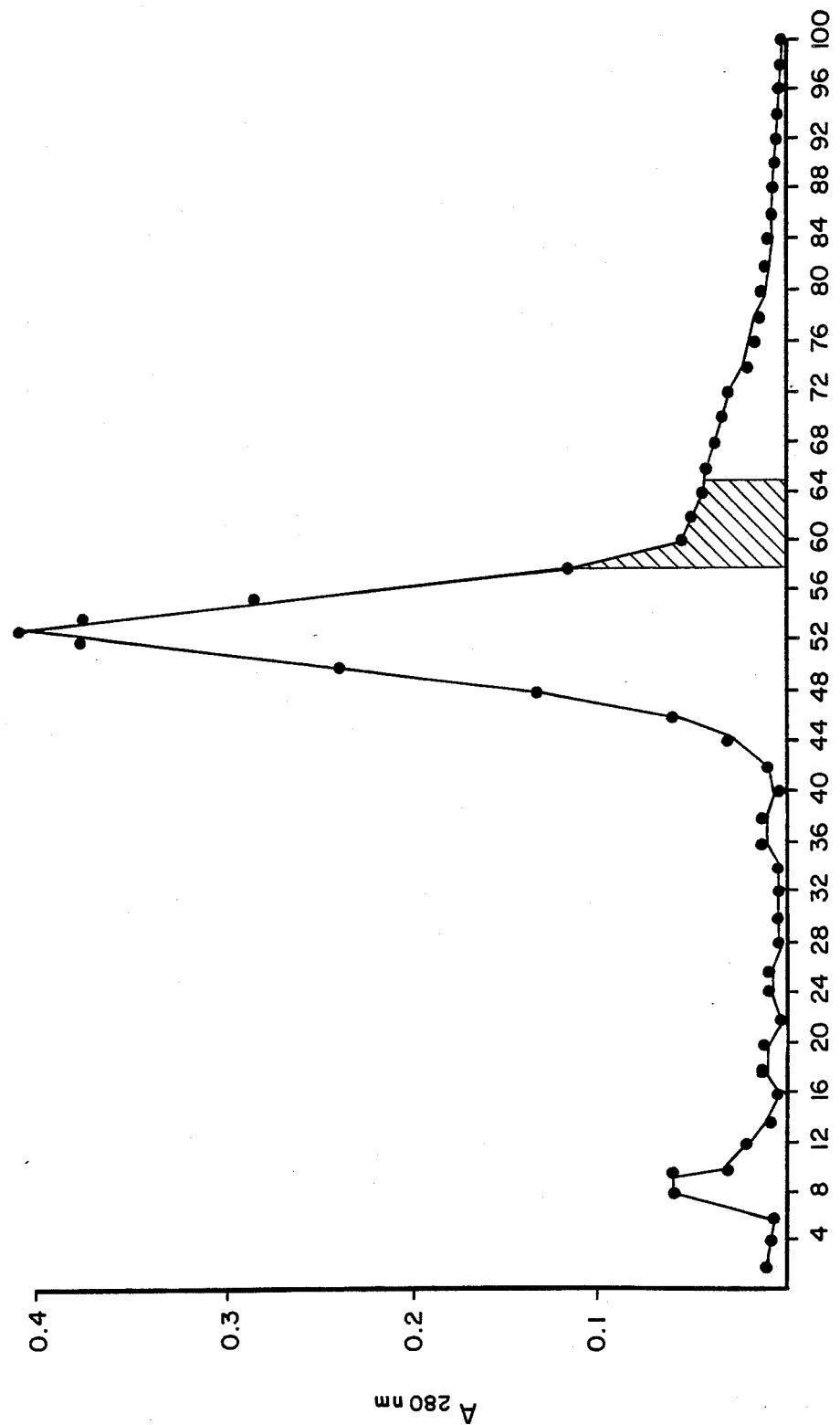

When the material which was retained by ultrafiltration (>10K fraction) was chromatographed on DEAE-Sephadex (after an additional two freeze-thaw cycles), in two experiments, the inhibitory activity was separated into a fraction which was not bound and one which was (FIG. 2, Table VI). If the high molecular weight fraction was passed over the strong anion exchanger QAE-Sephadex A-25, a small amount of inhibitory activity remained unbound, while the bulk of the inhibitory activity was bound and eluted in a position separated from hyaluronic acid (FIG. 3, Table VII). The material which did not bind to DEAE-Sephadex was subsequently chromatographed on the strong cation exchanger SP-Sephadex C-25. The inhibitory activity was strongly absorbed and was separated from the bulk of the protein applied to the column (FIG. 4,), The fractions within the shaded area produced an 84% inhibition of 3H-Thymidine incorporation into DNA.

111. Chromatofocusing of Vitreous Ultrafiltrate

As another method of testing the heterogeneity of the inhibitory activity present in the low molecular weight fraction of bovine vitreous and, as an additional purification method, chromatofocusing was chosen (Table VIII). When the vitreous ultrafiltrate was added to the PBE 94 column, one large and one small 280 nm-absorbing peak was removed by the starting buffer, 0.025M imidazole-HCl, ph 7.4. THe initial, larger peak had a slight inhibitory activity, while the second peak had no inhibitory activity. The addition of Polybuffer 74, which forms the ph gradient on the column, did not elute 280 nm-absorbing material until the pH had dropped to 5.3. A broad peak emerged, ending as the pH dropped below 4.3. The material in this fraction had a strong inhibitory effect on endothelial cell growth. A substance which was tightly bound to the column and was removed by a 1M NaCl wash being investigated further for cytotoxic effects.

TABLE I
Aortic Endothelial Cell Stimulatory Activity of Fresh Bovine Vitreous

| Fraction | Percent Concentration | CPM in DNA | Percent of Control |
|---|---|---|---|
| Control (0.15 M NaCl) | 40 | 90,812 ± 4,324 | — |
| 4–5 | 40 | 122,302 ± 11,310 | 135 |
| 6–7 | 40 | 128,148 ± 4,405 | 141 |

TABLE II
Aortic Endothelial Cell Growth Inhibitory Activity of High Molecular Weight* Fraction of Bovine Vitreous

| Fraction | Percent Concentration | CPM in DNA | Percent of Control |
|---|---|---|---|
| Control | 20 | 303,715 ± 2,700 | — |
| Vitreous | 20 | 269,232 ± 10,720 | 89 |
| Control | 40 | 337,568 ± 5,661 | — |
| Vitreous | 40 | 82,854 ± 10,281 | 25 |
| Control | 40 | 291,281 ± 9,572 | — |
| Vitreous+ | 40 | 244,705 ± 3,641 | 84 |
| Control | 20 | 241,545 ± 12,276 | — |
| Vitreous+ | 20 | 242,480 ± 1,470 | 100 |

*Bio Gel P-10 void volume fraction in 0.15 M NaCl.
+void volume fraction heated at 100° for 10 min prior to addition to cells.

TABLE III
Chromatography of Bovine Vitreous Ultrafiltrate* on Bio Gel P-10

| Elution Volume | CPM in DNA | Percent of Control |
|---|---|---|
| Control | 306,983 ± 52,274 | — |
| 302–312 ml | 213,338 ± 23,038 | 69 |
| Control | 387,946 ± 30,822 | — |
| 330–340 ml | 274,611 ± 21,040 | 71 |
| 341–350 | 232,141 ± 88,509 | 60 |
| Control | 291,300 ± 24,932 | — |
| 393–403 ml | 245,374 ± 4,739 | 84 |
| 404–414 | 194,652 ± 33,079 | 67 |
| 415–425 | 201,850 ± 22,748 | 69 |

*150 ml undialyzed bovine vitreous ultrafiltrate was concentrated to 10 ml in 3,500 dalton cutoff dialysis tubing, at 4° C., covered with Aquacide. The concentrate was chromatographed on a 3 cm × 82 cm preparative column of Bio Gel P-10, eluted with 0.15 M NaCl.

TABLE IV
CM-Sephadex Chromatography of Bovine Vitreous Ultrafiltrate

| Expt. | Fraction | CPM in DNA* |
|---|---|---|
| 1 | Control** | 310,848 ± 4,994 |
|   | 0.01 M KCl eluate+ | 90,444 ± 9,994 |
| 2 | Control | 281,890 ± 16,976 |
|   | 0.01 M KCl eluate | 144,595 ± 12,633 |

*mean of duplicate cultures ± S.D.
**0.15 M NaCl added to cultures at same concentration as eluate
+eluate dialyzed in 3,500 dalton cutoff tubing, freeze dried and dissolved in 0.15 M NaCl prior to addition to cells.

TABLE V
DEAE-Sephadex Chromatography of Bovine Vitreous Ultrafiltrate

| Peak | Fraction* | CPM in DNA** | Percent of Control |
|---|---|---|---|
| — | Control+ | 271,280 ± 34,878 | — |
| I | 0.08–0.1 M KCl | 186,128 ± 18,263 | 69 |
| II | 0.18–0.4 M KCl | 127,178 ± 48,988 | 47 |
| III | 0.45–0.65 M KCl | 190,655 ± 3,776 | 71 |

*Each fraction was dialyzed in 3,500 dalton cutoff tubing, freeze dried and dissolved in 0.15 M NaCl.
**mean ± S.D. of duplicate cultures
+control cultures received 0.15 M NaCl at same concentration as column fractions.

TABLE VI
DEAE-Sephadex Chromatography of Bovine Vitreous High Molecular Weight Inhibitor

| Peak | Fraction | CPM in DNA* | Percent of Control |
|---|---|---|---|
| A | Control+ | 381,359 ± 35,339 | — |
|   | 0.01 M KCl** | 261,147 ± 18,847 | 68 |
| B | Control | 267,263 ± 31,005 | — |
|   | 0.1 M–0.35 M KCl | 165,988 ± 2,105 | 62 |

*mean ± S.D. of duplicate cultures
+control cultures received equal concentrations of 0.15 M NaCl.
**column eluates were dialyzed, freeze dried and dissolved in 0.15 M NaCl.

TABLE VII
QAE-Sephadex Chromatography of High Molecular Weight Bovine Vitreous Inhibitor

| Peak | KCl (M) | Percent of Control |
|---|---|---|
| I | 0.01–0.015 | 65.8 |
| II | 0.02 | 80.1 |
| III | 0.06–0.08 | 65.9 |
| IVa | 0.08–0.15 | 68.0 |
| IVb | 0.15–0.7 | 116.6 |
| V | 0.7–1.2 | 121.4 |

TABLE VIII
Chromatofocusing of Vitreous Ultrafiltrate

|   | CPM in DNA* | Percent of Control |
|---|---|---|
| Control 0.15 M NaCl | 10,785 ± 2,019 | — |
| pH 7.4 | 7,959 ± 711 | 74 |
| pH 7.4 | 10,125 ± 2,218 | 94 |
| pH 5.3–4.3 | 5,273 ± 2,513 | 49 |
| 1 M NaCl | 615 ± 1 | 6 |

100 mg of bovine vitreous ultrafiltrate was dissolved in 2 ml 0.025 M imidazole, pH 7.4 and applied to a column of PBE 94. Elution was carried out as described in Methods. The material eluting between pH 5.3–4.3 and the 1 M NaCl eluate were both lyophilized, dissolved in 0.15 M NaCl and passed over a column of Sephadex G-75 (see Methods) to separate protein from Polybuffer 74. All fractions were dialyzed against distilled water, lyophilized and dissolved in 0.15 M NaCl prior to testing on aortic endothelial cells. Control cells received 0.15 M NaCl.
*mean of duplicate incubations ± S.D.

I claim:

1. A method for preparing an inhibitor of cell growth, comprising freezing vitreous gel for a sufficient time so as to inactivate growth stimulators that may be present, directly liquifying the gel in the absence of extraction solvent by application of shear forces to the gel so as to directly convert the gel into a liquid, removing any insoluble and suspended material from the liquid, chromatographically separating the liquid into fractions of varying molecular weight and isolating a product of molecular weight in excess of 10,000 daltons which has inhibitory activity.

2. The method of claim 1 wherein the product inhibits growth of endothelial cells.

3. The method of claim 1 wherein the vitreous gel is of animal orgin.

4. The method of claim 1 wherein the vitreous gel is of human orgin.

5. The method of claim 1 wherein the liquid is separated into fractions by liquid chromatography utilizing an eluent.

6. The method of claim 1 wherein the liquid is separated into fractions by ultrafiltration and then liquid chromatography utilizing an eluent.

7. The method of claim 5 wherein the eluent is physiological saline.

8. The method of claim 6 wherein the eluent is physiological saline.

9. An inhibitor of cell growth made by the method of claim 1.

10. An inhibitor of cell growth made by the method of claim 3.

11. An inhibitor of cell growth made by the method of claim 4.

12. An inhibitor of cell growth made by the method of claim 5.

13. An inhibitor of cell growth made by the method of claim 6.

14. A method of treating or preventing ocular neovascularization comprising the administration to ocular tissue of the inhibitor of claim 9.

15. A method of reducing neovascularization in a tumor comprising the administration to the tumor of the inhibitor of claim 9.

* * * * *